United States Patent [19]

Hoover et al.

[11] Patent Number: 4,859,654

[45] Date of Patent: Aug. 22, 1989

[54] HOMOCYCLOSTATINE AND CYCLOSTATINE CONTAINING POLYPEPTIDES AS ANTIHYPERTENSIVE AGENTS

[75] Inventors: Dennis J. Hoover, Ledyard; Robert L. Rosati, Stonington, both of Conn.

[73] Assignee: Pfizer Inc., New York, N.Y.

[21] Appl. No.: 200,820

[22] Filed: Jun. 1, 1988

Related U.S. Application Data

[63] Continuation-in-part of Ser. No. 68,992, Jul. 1, 1987.

[51] Int. Cl.[4] ............... A61K 37/00; C07K 5/06; C07K 5/08
[52] U.S. Cl. .................................. 514/19; 514/18; 530/331; 530/332; 530/323
[58] Field of Search ............ 530/330, 331, 332, 323; 514/18, 19

[56] References Cited

U.S. PATENT DOCUMENTS

| 4,638,047 | 1/1987 | Szelke et al. | 530/328 |
| 4,698,329 | 10/1987 | Matsueda et al. | 530/331 |
| 4,705,846 | 11/1987 | Thaisrivongs | 530/328 |
| 4,729,985 | 3/1988 | Kleinman et al. | 530/323 |

FOREIGN PATENT DOCUMENTS 0220665 10/1986 European Pat. Off. .
8704349 7/1987 European Pat. Off. .

Primary Examiner—Delbert R. Phillips
Attorney, Agent, or Firm—Peter C. Richardson; J. Trevor Lumb; James M. McManus

[57] ABSTRACT

Polypeptides and derivatives thereof containing homocyclostatine and cyclostatine are useful for inhibiting the angiotensinogen-cleaving action of the enzyme renin.

12 Claims, No Drawings

HOMOCYCLOSTATINE AND CYCLOSTATINE CONTAINING POLYPEPTIDES AS ANTIHYPERTENSIVE AGENTS

CROSS REFERENCE TO RELATED APPLICATION

This application is a continuation-in-part of copending application Ser. No. 068,992, filed July 1, 1987.

BACKGROUND OF THE INVENTION

This invention relates to novel homocyclostatine and cyclostatine containing polypeptides useful and antihypertensive agents.

The proteolytic enzyme renin, which has a molecular weight of about 40,000, is produced in and secreted into the blood by the kidney. It is known to be active vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

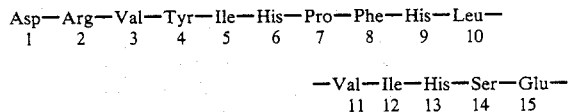

circulating N-terminal decapeptide (angiotensin I) formed by the above cleaving action of renin is subsequently broken down by the body to an octapeptide known as angiotensin II. Angiotensin II is known to be a potent pressor substance, i.e. a substance that is capable of inducing a significant increase in blood pressure and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known including antirenin antibodies, pepstatin and naturally-occurring phospholipid compounds. European Patent Application No. 45,665 (published Feb. 2, 1982) discloses a series of renin-inhibiting polypeptide derivatives of the formula X-Y-Pro-Phe-His-A-B-Z-W in which X may be hydrogen or an amino-protecting group, Y may be absent, B is a lipophilic amino acid residue, Z is an aromatic amino acid residue, W may be hydroxyl and A may be, inter alia,

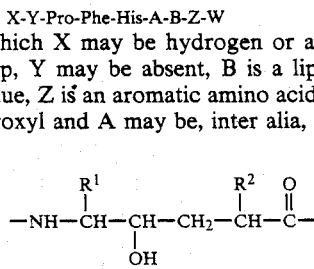

with each of $R^1$ and $R^2$ being a lipophilic or aromatic side chain. According to the definitions set forth in this published patent application, it is not contemplated that either A or Z could be statine or that B could be lysine.

European Patent Application No. 77,028A (published Apr. 20, 1983) discloses a series of renin-inhibiting polypeptide compounds having a non-terminal statine or statine derivative residue. Included within this series are compounds having a phenylalanine-histidine-statine sequence.

European Patent Application No. 132,304A also discloses the use of statine containing polypeptides as renin-inhibiting antihypertensive agents, and European Patent Application No. 114,993A discloses polypeptides containing cyclostatine, useful as renin-inhibiting antihypertensive agents.

SUMMARY OF THE INVENTION

The novel peptides of the present invention are of the formula

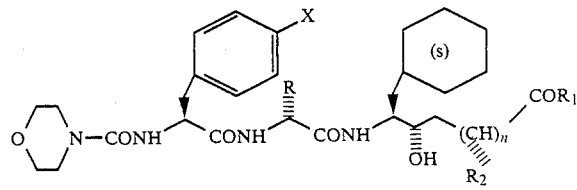

and a pharmaceutically acceptable salt thereof wherein X is hydrogen, methoxy or hydroxy; R is alkyl of one to six carbon atoms, imidazol-4-ylmethyl or methylthiomethyl; n is an integer of 0 or 1; $R_1$ is amino, alkylamino of one to five carbon atoms, alkoxy of one to three carbon atoms or 2-alkoxycarbonylpyrrolidin-1-yl, said alkoxy having from one to three carbon atoms; and $R_2$ is alkyl having from three to four carbon atoms, $-CH_2CH(Cl)=CH_2$, $-CH_2CH=CHCH_2N_3$, $-(CH_2)_4NH_2$, $-CH_2CH(Br)=CH_2$, $-CH_2CH=CHCl$, $-CH_2CH=C(CH_3)_2$, $-CH_2CH=CHCH_3$ or $-CH_2C\equiv CH$.

A preferred group of compounds are those where X is hydrogen and R is alkyl having three to four carbon atoms. Especially preferred in this group are the compounds where R is n-butyl, n is 1, $R_1$ is methylamino and $R_2$ is i-butyl, where R is n-butyl, n is 0 and $R_1$ is amino, where R is n-butyl, n is 0 and $R_1$ is methoxy, where R is n-butyl, n is 0 and $R_1$ is 2-methylbutylamino and where R is n-butyl, n is 0 and $R_1$ is 2-methoxycarbonylpyrrolidin-1-yl.

A second preferred group of compounds are those where X is hydrogen and R is imidazol-4-ylmethyl. Especially preferred within this group are the compounds where n is 1, $R_1$ is methylamino and $R_2$ is i-butyl, where n is 0 and $R_1$ is methylamino and where n is 0 and $R_1$ is methoxy.

A third preferred group of compounds are those where X is hydrogen, R is alkyl having three to four carbon atoms and n is 1. Especially preferred within this group is the compound where $R_1$ is methylamino and $R_2$ is $-CH_2CH(Cl)=CH_2$.

A fourth preferred group of compounds are those where X is hydrogen, n is 0 and $R_1$ is alkoxy having one to three carbon atoms. Especially preferred within this group is the compound where $R_1$ is methoxy and R is methylthiomethyl.

The present invention also includes a method for treating hypertension in a mammal which comprises treating said mammal with an antihypertensive effective amount of a compound of the present invention, and a pharmaceutical composition comprising an antihypertensive effective amount of a compound of the present invention and a pharmaceutically acceptable diluent or carrier.

As previously indicated, the present invention embraces pharmaceutically acceptable salts of the biologically active compounds. Such salts are those which are non-toxic at the dosages administered. Since compounds of the invention may contain basic groups, acid addition salts are possible. Pharmaceutically acceptable acid addition salts include e.g. the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts.

In the interest of brevity, the commonly accepted abbreviated name of the individual amino acids have been employed where possible. For example, the amino acid phenylalanine is abbreviated as Phe, histidine as His, lysine as Lys, and norleucine as Nle, etc. The amino protecting group t-butoxycarbonyl is abbreviated as Boc, benzyloxycarbonyl as CBZ and N-t-butoxycarbonyl on the imidazole of histidine as imBoc Cyclostatine and homocyclostatine, which contains one more carbon atom in the structure, are of the formula

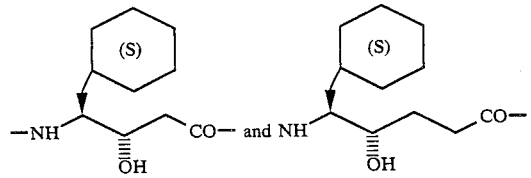

These structures are abbreviated as C-Sta and homo-C-Sta, respectively.

All the natural amino acid contained in the structures of the instantly claimed compounds are of the L configuration, the naturally occurring configuration, unless otherwise noted.

Further, the present invention includes compounds of the formula

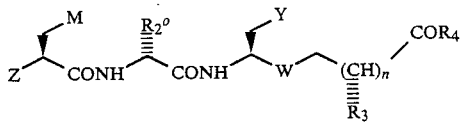

where Z is $R_5$—$(A)_m$—$(B)_p$— where $R_5$ is $(C_1-C_4)$alkoxy, $(C_1-C_4)$alkylamino di-$(C_1-C_4)$alkylamino, hydroxy $(C_1-C_4)$alkylamino, $(C_1-C_4)$alkoxyCOCH$_2$N(CH$_3$)—, morpholino, piperidino, piperazino, 4-methylpiperazino, thiomorpholino, thiomorpholino sulfoxide, thiomorpholino sulfone, 3-oxomorpholino, 3,5-dioxomorpholino, 4-$(C_1-C_4)$alkanoylpiperazino, 4-$(C_1-C_4)$alkoxycarbonylpiperazino, N-proline$(C_1-C_4)$alkyl ester or alkoxy $(C_1-C_4)$alkylamino; A is C=O,

or SO$_2$; B is NH or O; m and p are each 0 or 1;

M is phenyl, benzyl or naphthyl;

$R_2°$ is alkyl of one to five carbons, alkylthioalkyl of two to four carbons, alkoxyalkyl of two to four carbons, alkylsulfonylalkyl of two to four carbons, alkylsulfinylalkyl of two to four carbons, imidazol-4-ylmethyl;

Y is t-butyl, phenyl, i-propyl or cyclohexyl;

W is C=O or C(H)|||OH;

$R_3$ is $(C_1-C_5)$alkyl, $(C_6-C_8)$cycloalkylalkyl, 4-aminobutyl, CH$_2$C(Cl)=CH$_2$, CH$_2$C(Br)=CH$_2$ or CH$_2$CH=CH—CH$_2$N$_3$; and $R_4$ is alkoxy having one to four carbon atoms, alkylamino having one to four carbon atoms, aminoalkylamino having two to five carbon atoms, trifluoroethylamino, carboxy$(C_1-C_4)$alkylamino, amino, di$(C_1-C_4)$alkylamino or allylamino, with the proviso that when m is 0, p is 0 and when B is O, A is C=O.

DETAILED DESCRIPTION OF THE INVENTION

The compound of this invention exhibit antihypertensive activity in vivo in mammals, including humans. At least a substantial portion of this actvity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selected for renin. Because of their low molecular weights they exhibit favorable solubilizing characteristics in aqueous media, thus making oral administration feasible, and can be synthesized at a commercially realistic cost. The compounds of the present invention are also useful against congestive heart failure.

The compounds of the invention may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end as described herein. The amino acids utilized to synthesize the compounds of the present invention are commercially available (as free acids, salts or esters, etc.) in both alpha-amino protected and alpha-amino unprotected forms.

The activity of the compounds of the present invention as inhibitors of the angiotensinogen-cleaving activity of renin may be determined by studying their ability to inhibit the angiotensinogen-cleaving activity of renin in vitro.

The compounds of the present invention can be administered as antihypertensive agents by either the oral or parental routes of administration, with the former being preferred for reasons of patient convenience and comfort. In general, these antihypertensive compounds are normally administered orally in dosage ranging from about 0.5 mg to about 50 mg per kg of body weight per day and 0.1 mg to about 5 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carrier in the form of tablets, capsules, lozenges, troches, hard candies, powders, sprays, aqueous suspensions, elixirs, syrups and the like. Such carriers included solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatin and acacia. Additionally, lubricating agents such as magnesium stearate, sodium lauryl sulfate and talc are compositions of a similar type may also be employed as fillers in soft and hard-filled gelatin capsules; included lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or as water, ethanol, propylene glycol, glycerin and various like combinations thereof.

The following examples illustrate the invention but are not to be construed as limiting the same.

General Experimental

High performance liquid chromatography (HPLC) was performed with the following conditions: 214 nm detection, 4.6×250 mm Dupont Zorbax C-8 column at 1.5 ml/min. TLC systems are abbreviated as follows: System A=ethyl acetate-hexane, respectively, in the ratio indicated, on silica; System B=ether-hexane, respectively, in the ratio indicated, on silica; System C=18/2/1 HCCl$_3$-EtOH-HOAc on silica, System D=9:2:1 chloroform-ethanol-acetic acid.

EXAMPLE 1

MorpholinocarbonylPheHis-2-isobutylhomo-C-Sta N-methylamide (X=H, n=1, R=imidazol-4-ylmethyl, R$_1$=NHCH$_3$ and R$_2$=—CH$_2$CH(CH$_3$)$_2$)

A. di-t-butoxycarbonyl histidine benzyl ester

N$_\alpha$-t-Boc-N$_\pi$-Boc-L-histidine (113.4 g) was dissolved in 800 ml dry dimethylformamide and the stirred solution treated at 0° C. with 43.9 g anhydrous potassium carbonate and 37.8 ml benzyl bromide. The mixture was stirred in an ice bath which was allowed to reach 20° C. overnight. The suspension was filtered through Celite which was washed with ether, the filtrates were concentrated and the residue dissolved in 700 ml ethyl acetate. This solution was washed with 2×200 ml of 1M aqueous lithium chloride, 100 ml of 4M aqueous lithium chloride, 2×100 ml 1N sodium hydroxide solution, water, brine, dried over magnesium sulfate and concentrated giving an oily solid which was stirred vigorously with 500 ml hexanes. The filtered solid was washed at 25° C. with 2×100 ml hexane and dried giving 120.5 g (85.5%) of the title substance as a colorless solid, m.p. 97°–99.5° C., [alpha]$_D^{25}$ −6.4° (c=1.09, CHCl$_3$), TLC Rf 0.35 in 1:1 ethyl acetate-hexane. Material twice recrystallized from 1:4 ethyl acetate-hexane showed m.p. 99°–106° C. and [alpha]$_D^{23}$ −6.6° (c=1.25, CHCl$_3$).

B. histidine benzyl ester hydrochloride

The product of Example 1A was dissolved in a solution of 56 g of anhydrous hydrogen chloride in 400 ml p-dioxane. The suspension was stirred at 25° C. for 24 hours. The mixture was concentrated, the residue washed with three portions of ether on the funnel and dried at 56° C. in vacuo for 10 hours giving 69.5 g of a colorless solid, [alpha]$_D^{25}$ +6.4° (c=2.865, MeOH) (reported, Org. Prep. Proc. Int'l 1970, 255, [alpha]$_D$=6.54°).

C. morpholinocarbonylPheHis benzyl ester

The product of Example 1B (1.37 g) was dissolved in 5 ml dichloromethane, cooled to 0° C. and treated sequentially with 555 µl (1.0 equiv) triethylamine, 1.21 g (1.05 equiv) morpholinocarbonylPhe, 928 mg of hydroxybenzotriazole hydrate and 780 mg dicyclohexylcarbodiimide. This mixture was stirred in an ice bath which was allowed to achieve 20° C. overnight. The mixture was filtered, the solids washed with dichloromethane and the filtrates were washed with 1N sodium hydroxide solution (2×), aqueous bicarbonate, brine, dried over magnesium sulfate and concentrated giving 1.8 g of a light yellow solid which was triturated with ether and dried to give 1.68 g (67%) of the title substance as a yellow solid.

D. morpholinocarbonylPheHis(imBoc) benzyl ester

The product of Example 1C (1.68 g) was dissolved in 30 ml p-dioxane and 15 ml water and the pH was raised to 11 by addition of 1N sodium hydroxide solution. Di-t-butyldicarbonate (850 µl) was added and the pH was maintained between 9 and 11 with added base. After 45 minutes another 450 µl of di-t-butyldicarbonate was added and the pH was maintained near 0.5. After 1.5 hours total, the pH was adjusted to 5 with 1N hydrochloric acid, the mixture was partially concentrated to remove the p-dioxane and the solution was extracted with ethyl acetate (4×100 ml). The combined organic layers were washed with 1N sodium hydroxide solution, aqueous bicarbonate, dried over sodium sulfate and concentrated giving 1.85 g of an oily foam which was chromatographed on 60 g silica eluting with 2%, 4%, 6% and 8% ethanol in dichloromethane, giving after concentration of the appropriate fractions 1.05 g of the title substance as a pale yellow foam, TLC Rf 0.13 in ethyl acetate.

E. morpholinocarbonylPheHis(imBoc)

A solution of 485 mg of the product of Example 1D in 25 ml 10:1 methanol-acetic acid was shaken with 200 mg 10% Pd/C for 30 minutes at 50 p.s.i. hydrogen pressure. The mixture was filtered through Celite which was washed with methanol-acetic acid, the filtrates concentrated, the residue coevaporated with ether and dried giving 361 mg (87%) of the title substance, Rf 0.25 in 18:2:1 chloroform-ethanol-acetic acid, as an off-white foam.

F. morpholinocarbonylPheHis(imBoc)-2-i-butylhomo-C-Sta lactone

A solution of 213 mg 2-isobutylhomo-C-Sta lactone hydrochloride (EPO Publication No. 0212903(A2)) in 1.5 ml dichloromethane was treated sequentially at 0° C. with 126 μl triethylamine, 361 mg of the product of Example 1E, 161 mg 1-hydroxybenzotriazole and 144 mg dicyclohexylcarbodiimide. The mixture was stirred overnight during which time the temperature rose to 20° C. The mixture was filtered, the precipitate washed with dichloromethane, the filtrates concentrated, and the residue dissolved in ethyl acetate. After being stirred for 15 minutes, the resulting suspension was filtered, and the filtrate was washed with 1N sodium hydroxide solution (2×), brine, dried over magnesium sulfate and concentrated giving 754 mg of an off-white foam which was chromatographed on 35 g silica packed in 0.5% ethanol-dichloromethane. The column was eluted with 0.5%, 1%, 2% and 4% ethanol-dichloromethane and the appropriate fractions were concentrated giving 396 mg (74%) of the title substance as a colorless foam, TLC Rf 0.63 in 18/2/1 chloroform-ethanol-acetic acid.

G. morpholinocarbonylPheHis-2-i-butylhomo-C-Sta N-methylamide

The product of Example 1F (361 mg) was dissolved in methanol (3 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was chromatographed on 20 g silica packed in 4% ethanol-dichloromethane. The column was eluted with 600 ml each of 4%, 6%, 12% and 15% ethanol-dichloromethane. Concentration of the appropriate fractions gave 296 mg (84%) of the title substance as a colorless powder, HPLC in 50/50 acetonitrile-buffer 3.23 minutes.

1H NMR (DMSO-d6, 300 mHz, δ, ppm, partial) 0.86 and 0.90 (d, 6H total), 0.97–1.80 (m, ca. 15H total), 2.40 (shoulder on DMSO peak), 2.51 (d, NCH$_3$), 2.66–3.0 (m, ca. 4H), 3.0–3.72 (m), 4.15 (m, 1H), 4.37 (m, 1H), 6.80 and 7.50 (s, 1H ea, imidazolyl CH), 7.60 and 8.47 (m, 1H ea). FAB-MS [thioglycerol, m/e (rel. intensity], 233(39), 250(14), 261(16), 283(17), 405(10), 642(16), 696(100, MH+), 697(47), 698(14).

EXAMPLE 2

MorpholinocarbonylPheNle-2-i-butylhomo-C-Sta N-methylamide (X=H, n=1, R=n-C$_4$H$_9$, R$_1$=NHCH$_3$ and R$_2$=—CH$_2$CH(CH$_3$)$_2$)

A. morpholinocarbonylPheNle-2-i-butylhomo-C-Sta lactone

According to the general procedure for preparation and purification of the product of Example 1F (replacing H is with Nle), 52 mg of 2-isobutyl-homo-C-Sta lactone hydrochloride was dissolved in 0.5 ml dichloromethane and treated with 34 μl triethylamine, 67 mg of morpholino-carbonylPheNle, 39 mg HBT and 35 mg DCC. After analogous reaction and isolation (chromatography was not necessary in this case), 103 mg of the title substance was isolated as a colorless foam, TLC Rf 0.69 in 18/2/1 HCCl$_3$-ethanol-HOAc.

B. morpholinocarbonylPheNle-2-i-butylhomo-C-Sta N-methylamide

According to the procedure for preparation and purification of the product of Example 1G, 102 mg of the product of Example 2A gave 77 mg (72%) of the title substance as a colorless powder, TLC Rf 0.5 in 18/2/1 HCCl$_3$-ethanol-HOAc, HPLC 2.85 minutes in 70/30 acetonitrile-buffer.

1H NMR (DMSO-d6, 300 mHz, δ, ppm, partial): 0.82–1.0 (m, 9–10H), 1.0–1.9 (m, ca. 24H), 2.46 (m, 1H), 2.57 (d, 3H, NCH$_3$), 2.86 (dd, 1H), 3.02 (dd, 1H), 3.26 (m, 4H), 3.51 (m, 4H), 3.78 (m, 1H), 4.22 (m, 2H), 4.59 (d, 1H), 6.70 (d, 1H), 7.14–7.44 (m, ca. 6H), 7.63 (m, 1H), 8.00 (d, 1H); FAB-MS [thioglycerol, m/e (rel. intensity)], 217(18), 233(61), 234(11), 250(13), 264(10), 268(17), 281(12), 299(21), 381(12), 394(14), 654(39), 655(25), 656(17), 670(12), 672(100, MH+), 673(40), 674(11).

EXAMPLE 3

MorpholiocarbonylPheNle-C-Sta methyl ester (X=H, n=0, R=CH$_3$(CH$_2$)$_3$— and R$_1$=OCH$_3$)

A. N-t-butoxycarbonyl-C-Sta methyl ester t-Butoxycarbonyl-C-Sta (315 mg, 1 mmole) was added to 20 ml of diethyl ether containing approximately 5 mmoles of diazomethane and the reaction mixture allowed to stir overnight at room temperature. Removal of the solvent gave 336 mg of the desired product as an oil.

B. C-Sta methyl ester hydrochloride

The product of Example 3A was added to 5 ml of dioxane saturated with hydrogen chloride and the reaction stirred at room temperature for 90 minutes. Removal of the solvent gave 279 mg of the desired compound as a foam.

C. morpholinocarbonylPheNle-C-Sta methyl ester

A mixture of 265 mg of the product of Example 3B, 101.2 mg of N-methylmorpholine, 391.5 mg of morpholinocarbonylPheNle, 135 mg of 1-hydroxybenzotriazole and 206 mg of dicyclohexylcarbodiimide in 20 ml of methylene chloride was stirred overnight at room temperature. The reaction mixture was filtered, washed with water and a saturated brine solution and the organic phase dried over sodium sulfate. Removal of the solvent in vacuo gave 528 mg of crude product, which was purified by chromatography on 53 g of silica gel using chloroform-methanol (99:1; v:v) as the eluent (4.5 ml fractions) for the first 160 fractions followed by chloroform-methanol (97.5:2.5;v:v) for the remainder of the collecting. The fractions containing the product were combined and concentrated to give 203 mg of pure product as a white solid.

1H NMR (DMSO-d6, 60 mHz, ppm partial) 1.00 (t, 3H, J=5Hz), 2.2–2.4 (d, 2H, J=5Hz), 3.2–3.4 (m, 4H), 3.45–3.60 (m, 4H), 3.8 (s, 3H), 7.2 (s, 5H).

EXAMPLE 4

MorpholinocarbonylPheNle-C-Sta N-2-methylbutyl amide (X=H, n=0, R=CH$_3$(CH$_2$)$_3$— and R$_1$=NHCH$_2$CH(CH$_3$)CH$_2$CH$_3$)

A. N-t-butoxycarbonyl-C-Sta N-2-methylbutyl amide

A solution of 80.6 mg of N-t-butoxycarbonyl-C-Sta in 50 ml of methylene chloride was treated with 22.3 mg of 2-methylbutylamine, 34.5 mg of 1-hydroxybenzotriazole and 52.7 mg of dicyclohexylcarbodiimide and the reaction mixture was stirred at 0° C. for 6 hours, then allowed to warm to room temperature overnight. The reaction was filtered and the precipitate washed with methylene chloride and combined with the original filtrate. The methylene chloride was removed in vacuo and the residue treated with ethyl acetate. The suspension was filtered and the filtrate concentrated to a foam, 116 mg.

B. C-Sta N-2-methylbutylamide hydrochloride

The product of Example 4A, 116 mg, was added to 5 ml of dioxane saturated with hydrogen chloride and the solution allowed to stir at room temperature for 90 minutes. The solution was concentrated in vacuo, 87 mg.

C. morpholinocarbonylPheNle-C-Sta N-2-methylbutyl amide

Following the general procedure of Example 1F, 87 mg of the product of Example 4B, 25.9 mg of N-methylmorpholine, 100 mg of morpholinocarbonylPheNle, 34.5 mg of 1-hydroxybenzotriazole and 52.7 mg of dicyclohexylcarbodiimide in 20 ml of methylene chloride gave 212 mg of crude product.

The product was purified by chromatography on 21 g of silica gel using chloroform-methanol (99:1; v:v) as the eluent for the first 80 fractions (4 ml) followed by chloroform-mehtanol (97.5:2.5; v:v). The fractions containing the product were combined and concentrated under vacuum to give 80 mg of pure product as a white solid.

1H NMR (DMSO-d$_6$, 60 mHz, ppm partial) 2.20 (d, 2H, J=5Hz), 3.2–3.4 (m, 4H), 3.6–3.8 (m, 4H), 7.25 (s, 5H).

EXAMPLE 5

MorpholinocarbonylPheNle-C-StaPro methyl ester (X=H, n=0, R=CH$_3$(CH$_2$)$_3$— and R$_1$=2-methoxycarbonylpyrrolidin-1-yl)

A. N-t-butoxycarbonyl-C-StaPro methyl ester

Using the general procedure of Example 1F, 41.3 mg of proline methyl ester hydrochloride, 25.3 mg of N-methylmorpholine, 78.8 mg of N-t-butoxycarbonyl-C-Sta, 33.8 mg of 1-hydroxybenzotriazole 51.5 mg of dicyclohexylcarbodiimide in 20 ml of methylene chloride gave 124 mg of product.

B. C-StaPro methyl ester hydrochloride

Following the procedure of Example 1B, the product of Example 5A gave, after a reaction time of 90 minutes, 102 mg of the titled product.

C. morpholinocarbonylPheNle-C-StaPro methyl ester

Employing the product of Example 5B, 25.3 mg of N-methylmorpholine, 97.8 mg of morpholinocarbonylPheNle, 33.8 mg of 1-hydroxybenzotriazole and 51.5 mg of dicyclohexylcarbodiimide in 20 ml of methylene chloride, and following the procedure of Example 1F, 157 mg of the product was obtained.

The product was chromatographed on 16 g of silica gel using a chloroform-methanol eleuent (99:1; v:v) for the first 80 fractions (4 ml) followed by chloroform-methanol (97.5:2.5, v:v). The fractions containing the product were combined and concentrated to dryness, 82 mg.

1H NMR (DMSO-d$_6$, 60 mHz, ppm partial) 1.0 (t, 3H, J=5Hz), 2.2 (d, 2H, J=5Hz), 3.2–3.4 (m, 4H), 3.5–3.7 (m, 4H), 3.85 (s, 3H), 7.2 (s, 5H).

EXAMPLE 6

MorpholinocarbonylPheHis-C-Sta methyl ester (X=H, n=0, R=imidazol-4-ylmethyl and R$_1$=OCH$_3$)

A di-t-butoxycarbonylHis-C-Sta methyl ester

Using the procedure of Example 1F, 82.6 mg of C-Sta methyl ester hydrochloride, 32.1 mg of N-methylmorpholine, 112.7 mg of di-t-butoxycarbonyl L-histidine, 42.9 mg of 1-hydroxybenzotriazole and 65.4 mg of dicyclohexylcarbodiimide in 20 ml of methylene gave 221 mg of the crude product.

B. His-C-Sta methyl ester dihydrochloride

Following the general procedure of Example 1B, the product of Example 6A in 10 ml of dioxane saturated with hydrogen chloride after 2 hours gave 146 g of product on work-up.

C. morpholinocarbonylPheHis-Sta methyl ester

Again, following the coupling procedure of Example 1F, 146 mg of the product of Example 6B, 64.2 mg of N-methylmorpholine, 88.3 mg of morpholinocarbonyl-Phe, 42.9 mg of 1-hydroxybenzotriazole and 65.4 mg of dicyclohexylcarbodiimide in 20 ml of methylene chloride gave on work-up 206 mg of product.

The product was purified by chromatographing on 21 g of silica gel using chloroform-methanol (99:1; v:v) as an eluent for the first 160 fractions (4 ml) followed by chloroform-methanol (95:5; v:v) thereafter. The fractions containing the product were combined and concentrated in vacuo, 38.6 mg.

1H NMR DMSO-d$_6$, 60 mHz, ppm partial) 1.0 (t, 3H, J=5Hz), 2.25 (d, 2H, J=5Hz), 3.2–3.4 (m, 2H), 3.5–3.7 (m, 2H), 3.8 (s, 3H), 6.8 (s, 1H), 7.2 (s, 5H), 7.5 (s, 1H).

EXAMPLE 7

MorpholinocarbonylPheNle-C-Sta amide (X=H, n=0, R=CH$_3$(CH$_2$)$_3$— and R$_1$=NH$_2$)

A solution of 90 mg of the product of Example 3 in 10 ml of methanol as saturated with ammonia and allowed to stir at room temperature for several days. The solution was resaturated and allowed to stir for several more days. The excess ammonia and methanol were removed in vacuo and the residue triturated with ether and filtered, 65 mg.

1H NMR (DMSO-d$_6$, 60 mHz, ppm partial) 1.0 (t, 3H, J=5Hz), 2.2 (d, 2H, J=5Hz), 3.25–3.45 (m, 4H), 3.5–3.7 (m, 4H), 7.2 (s, 5H).

EXAMPLE 8

MorpholinocarbonylPheNle-C-Sta N-methyl amide (X=H, n=0, R=CH$_3$(CH$_2$)$_3$— and R$_1$=NHCH$_3$)

The procedure of Example 7 was repeated using 40 mg of the product of Example 3 and 10 ml of methanol saturated with methylamine to give, after a reaction time of several days at room temperature, 36 mg of the desired product.

1H NMR (DMSO-d$_6$, 60 mHz, ppm partial) 1.05 (t, 3H, J=5Hz), 2.3 (d, 2H, J=5Hz), 2.63 (s, 3H), 3.2–3.4 (m, 4H), 3.6–3.8 (m, 4H), 7.2 (s, 5H).

EXAMPLE 9

MorpholinocarbonylPheHis-C-Sta N-methyl amide (X=H, n=0, R=imidazol-4-ylmethyl and R$_1$=NHCH$_3$)

The procedure of Example 7 was followed starting with 33 mg of the product of Example 6 and 5 ml of methanol saturated with methylamine to give, after a reaction period of several days at room temperature, 20 mg of product.

1H NMR (DMSO-d$_6$, 60 mHz, ppm partial) 1.0 (t, 3H J=5Hz), 2.2 (d, 2H, J=5Hz), 2.65 (s, 3H), 3.2–3.4 (m, 4H), 3.5–3.7 (m, 4H), 6.8 (s, 1H), 7.2 (s, 5H), 7.6 (s, 1H).

EXAMPLE 10

MorpholinocarbonylPheNle-2-(2'-chloro-2'-propenyl)-homo-C-Sta N-methylamide (X=H, R=CH$_3$(CH$_2$)$_3$—, R$_1$=NHCH$_3$ and R$_2$=—CH$_2$CH(Cl)=CH$_2$)

A. morpholinocarbonylPheNle-2-(2'-chloro-2'-propenyl)-homo-C-Sta lactone

The procedure of Example 1F was repeated using 57 mg of 2-(2'-chloro-2'-propenyl)homo-C-Sta lactone in 15 ml of dichloromethane, 19.5 μl of N-methylmorpholine, 69.8 mg of morpholinocarbonylPheNle, 23.9 mg of 1-hydroxybenzotriazole and 36.5 mg of cyclohexylcarbodiimide to give 88 mg of a foam which was chromatographed on 10 g of silica packed in chloroform. The column was eluted with chloroform and 99% chloroform-methanol (v:v), and the appropriate fractions combined and concentrated to give 43 mg of product.

B. morpholinocarbonylPheNle-2-(2'-chloro-2'-propenyl)-homo-C-Sta N-methylamide The product of Example 10A (43 mg) was dissolved in methanol (5 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 33 mg of the title substance as a colorless powder, $^1$H-NMR (DMSO-d$_6$, 300 mHz, δ, ppm, partial): 2.5 (d, NCH$_3$), 3.4 (m, 4H), 3.6 (m, 4H); 5.15 (m, 2H).

EXAMPLE 11

MorpholinocarbonylPheNle-2-(4'-azido-2'-butenyl)-homo-C-Sta N-methylamide (X=H, R=CH$_3$(CH$_2$)$_3$—, R$_1$=CH$_3$ and R$_2$=—CH$_2$CH=CHCH$_2$N$_3$)

A. morpholinocarbonylPheNle-2-(4'-azido-2'-butenyl)-homo-C-Sta lactone

A solution of 97 mg 2-(4'-azido-2'-butenyl)homo-C-Sta lactone hydrochloride in 20 ml dichloromethane was treated sequentially at 0° C. with 28 μl N-methylmorpholine, 110.6 mg of morpholinocarbonylPheNle, 38.2 mg 1-hydroxybenzotriazole and 58.3 mg dicyclohexylcarbodiimide. The mixture was stirred overnight during which time the temperature rose to 20° C. The mixture was filtered, the precipitate washed with dichloromethane, the filtrates concentrated and the residue dissolved in ethyl acetate. After being stirred for 15 minutes, the resulting suspension was filtered, and the filtrate was washed with 1N sodium hydroxide solution (2×), brine, dried over magnesium sulfate and concentrated giving 221 mg of an off-white foam which was chromatographed on 22 g silica packed in chloroform. The column was eluted with 99% chloroform-methanol and the appropriae fractions were concentrated giving 121 mg of the title substance as a colorless foam.

B. morpholinocarbonylPheNle-2-(4'-azido-2'-butenyl)-homo-C-Sta N-methylamide The product of Example 11A (121 mg) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 88 mg of the title substance as a colorless powder, $^1$H-NMR (DMSO-d$_6$, 300 mHz, δ, ppm, partial): 2.5 (d, NCH$_3$), 3.4 (m, 4H), 3.6 (m, 4H).

EXAMPLE 12

MorpholinocarbonylPheNle-2-(4'-amino-1'-butyl)-homo-C-Sta N-methylamide (X=H, R=CH$_3$(CH$_2$)$_3$, R$_1$=NHCH$_3$ and R$_2$=—CH$_2$)$_4$NH$_2$)

The product of Example 11B (58 mg) was hydrogenated at 50 psi in methanol in the presence of 20 mg of 5% palladium hydroxide on carbon for 19 hours at 25° C. The reaction after filtration was evaporated to dryness to afford (after ether trituration) 44 mg of the title compound. $^1$H-NMR (DMSO-d$_6$, 300 mHz, δ, ppm, partial): 2.5 (d, NCH$_3$), 3.4 (m, 4H), 3.6 (m, 4H).

EXAMPLE 13

MorpholinocarbonylPheNle-2-(2'-bromo-2'-propenyl)-homo-C-Sta N-methylamide (X=H, R=CH$_3$)CH$_2$)$_3$—, R$_1$=NHCH$_3$ and R$_2$=CH$_2$CH(Br)=CH$_2$)

A. morpholinocarbonylPheNle-2-(2'-bromo-2'-propenyl)-homo-C-Sta lactone

A solution of 78 mg 2-(2'-bromo-2'-propenyl)homo-C-Sta lactone hydrochloride in 20 ml dichloromethane was treated sequentially at 0° C. with 22 μl N-methylmorpholine, 78.2 mg of morpholinocarbonylPheNle, 27 mg 1-hydroxybenzotriazole and 41.2 mg dicyclohexylcarbodiimide, The mixture was stirred overnight during which time the temperature rose to 20° C. The mixture was filtered, the precipitate washed with dichloromethane, the filtrate concentrated, and the residue dissolved in ethyl acetate. After being stirred by 15 minutes, the resulting suspension was filtered, and the filtrate was washed with 1N sodium hydroxide solution (2x), brine dried over magnesium sulfate and concentrated giving 190 mg of an off-white foam which was chromatographed on 10 g silica packed in chloroform. The column was eluted and the appropriate fractions were concentrated giving 78 mg of the title substance as a colorless foam, TLC Rf 0.85 in 9/1 chloroform-methanol.

B.
morpholinocarbonylPheNle-2-(2'-bromo-2'-propenyl)-homo-C-Sta N-methylamide

The product of Example 13A (78 ml) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with either to give 55 mg of the title substance as a colorless powder, $^1$H-NMR (DMSO-d$_6$, 300 mHz, δ, ppm, partial): 2.5 (d, NCH$_3$), 3.4 (m, 4H), 3.6 (m, 4H), 5.5 (m, 2H).

EXAMPLE 14

MorpholinocarbonylPheNle-2-(3'-chloro-2'-propenyl)homo-C-Sta N-methylamide (X=H, R=CH$_3$(CH$_2$)$_3$, R$_1$=NHCH$_3$ and R$_2$=—CH$_2$CH=CHCl)

A.
morpholinocarbonylPheNle-2-(3'-chloro-2'-propenyl)-homo-C-Sta lactone

A solution of 136 mg 2-(3'-chloro-2'-propenyl)-homo-C-Sta lactone hydrochloride in 15 ml dichloromethane was treated sequentially at 0° C. with 21.4 μl N-methylmorpholine, 76 mg of morpholinocarbonylPheNle, 26.2 mg 1-hydroxybenzotriazole and 40 mg dicyclohexylcarbodiimide. The mixture was stirred overnight during which time the temperature rose to 20° C. The mixture was filtered, the precipitate washed with dichloromethane, the filtrates concentrated and the residue dissolved in ethyl acetate. After being stirred for 15 minutes, the resulting suspension was filtered, and the filtrate was washed with 1N sodium hydroxide solution (2x), brine, dried over magnesium sulfate and concentrated giving 167 mg of an off-white foam which was chromatographed on 17 g silica packed in chloroform. The column was eluted with chloroform and 99% chloroform-methanol and the appropriate fractions were concentrated giving 103 mg of the title substance as a colorless foam, TLC Rf 0.9 in 9/1 chloroformmethanol.

B.
morpholinocarbonylPheNle-2-(3'-chloro-2'-propenyl)-homo-C-Sta N-methylamide

The product of Example 14A (103 mg) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 4 mg of the title substance as a colorless powder, $^1$H-NMR (DMSO-d$_6$ 300 mHz, δ, ppm, partial): 2.5 (d, NCH$_3$), 3.4 (m, 4H), 3.6 (m, 4H), 5.6–6.4 (m, 2H).

EXAMPLE 15

MorpholinocarbonylPheNle-2-(3',3'-dimethyl-2'-propenyl)homo-C-Sta N-methylamide (X=H, R=CH$_3$(CH$_2$)$_3$—, R$_1$=NHCH$_3$ and R$_2$=—CH$_2$CH=C(CH$_3$)$_2$)

A.
morpholinocarbonylPheNle-2-(3',3'-dimethyl-2'-propenyl)homo-C-Sta lactone

A solution of 132 mg 2-(3',3'-dimethyl-2'-propenyl)-homo-C-Sta lactone hydrochloride in 15 ml dichloromethane was treated sequentially at 0° C. with 21.7 μl N-methylmorpholine, 77.3 mg of morpholinocarbonylPheNle, 26.7 mg 1-hydroxybenzotriazole and 40.7 mg dicyclohexylcarbodiimide. The mixture was stirred overnight during which time the temperature rose to 20° C. The mixture was filtered, the precipitate washed with dichloromethane, the filtrates concentrated, and the residue dissolved in ethyl acetate. After being stirred for 15 minutes, the resulting suspension was filtered, and the filtrate was washed with 1N-sodium hydroxide solution (2x), brine, dried over magnesium sulfate and concentrated giving 150 mg of an off-white foam which was chromatographed on 15 g silica packed in chloroform. The column was eluted with chloroform and 99% chloroform-methanol and the appropriate fractions were concentrated giving 89 mg of the title substance as a colorless foam, TLC Rf 0.6 in 9/1 chloroform-methanol.

B.
morpholinocarbonylPheNle-2-(3',3'-dimethyl-2'-propenyl)homo-C-Sta N-methylamide The product of Example 15A (89 mg) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 5 mg of the title substance as a colorless powder, $^1$H-NMR (DMSO-d$_6$, 300 mHz, δ, ppm, partial): 1.8 (br. s, 6H), 2.5 (d, NCH$_3$), 3.4 (m, 4H), 3.6 (m, 4H).

EXAMPLE 16

MorpholinocarbonylPheNle-2-(2'-butenyl)homo-C-Sta N-methylamide (X=H, R=CH$_3$(CH$_2$)$_3$, R$_1$=NHCH$_3$ and R$_2$=CH$_2$CH=CHCH$_3$)

A.
morpholinocarbonylPheNle-2-(2'-butenyl)homo-C-Sta lactone

A solution of 247 mg 2-(2'-butenyl)homo-C-Sta lactone hydrochloride in 15 ml dichloromethane was treated sequentially at 0° C. with 26.3 μl N-methylmorpholine, 93.4 mg of morpholinocarbonylPheNle, 32.3 mg 1-hydroxybenzotriazole and 49.2 mg dicyclohexylcarbodiimide. The mixture was stirred overnight during which time the temperature rose to 20° C. The mixture was filtered, the precipitate washed with dichloromethane, the filtrates concentrated, and the residue dissolved in ethyl acetate. After being stirred for 15 minutes, the resulting suspension was filtered, and the filtrate was washed with 1N sodium hydroxide solution (2x), brine, dried overmagnesium sulfate and concentrated giving 168 mg of an off-white foam which was chromatographed on 10 g silica packed in chloroform. The column was eluted with 99% chloroformmethanol and the appropriate fractions were concentrated giving 96 mg of the title substance as a colorless foam, TLC Rf 0.7 in 9/1 chloroform-methanol.

B.
morpholinocarbonylPheNle-2-(2'-butenyl)homo-C-Sta N-methylamide

The product of Example 16A (96 mg) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 66 mg of the title substance as a colorless powder, $^1$H-NMR (DMSO-d$_6$, 300 mHz, δ, ppm, partial): 1.8 (br.s, 3H); 2.5 (d, NCH$_3$), 3.4 (m, 4H), 3.6 (m, 4H).

EXAMPLE 17

MorpholinocarbonylPheNle-2-(propargyl)homo-C-Sta N-methylamide (x=H, R=CH$_3$(CH$_2$)$_3$—, R$_1$=NHCH$_3$ and R$_2$=CH$_2$C≡CH)

A. morpholinocarbonylPheNle-2-(3'-propargyl) homo-C-Sta lactone

A solution of 193 mg 2-(3'-propargyl)homo-C-Sta lactone hydrochloride in 15 ml dichloromethane was treated sequentially at 0° C. with 22.4 μl N-methylmorpholine, 83.2 mg of morpholinocarbonylPheNle, 28.7 mg 1-hydroxybenzotriazole and 43.8 mg dicyclohexylcarbodiimide. The mixture was stirred overnight during which time the temperature rose to 20° C. The mixture was filtered, the precipitate washed with dichloromethane, the filtrates concentrated, and the residue dissolved in ethyl acetate. After being stirred for 15 minutes, the resulting suspension was filtered, and the filtrate was washed with 1N sodium hydrodie solution (2x), brine, dried over magneisum foam which was chormatographed on 10 g silica packed in chloroform. The column was eluted with 99% chloroform-methanol and the appropriate fractions were concentrated giving 98 mg of the title substance as a colorless foam, TLC Rf 0.6 in9/1 chloroform-methanol.

B. morpholinocarbonylPheNle-2-(3'-propargyl)-homo-C-Sta N-methylamide

The product of Example 17A (98 mg) was dissolved in methanol (10 ml) and the resulting solution was saturated at 0° C. with anhydrous methylamine. The flask was stoppered and the solution was allowed to stand at 25° C. for 70 minutes. The solvent and excess methylamine were removed at reduced pressure and the resulting powder was triturated with ether to give 90 mg of the title substance as a colorless powder, $^1$H-NMR (DMSOd-$_6$, 300 mHz, δ, ppm, partial): 2.3 (m, 2H), 2.5 (d, NCH$_3$), 3.4 (m, 4H), 3.6 (m, 4H).

EXAMPLE 18

MorpholinocarbonylPhe S-MeCys-C-Sta Methyl Ester (X=H, n=0, R=CH$_2$SCH$_3$ and R$_1$=OCH$_3$)

A mixture of 135 mg of the product of Example 3B, 51 mg of N-methylmorpholine, 209 mg of morpholinocarbonylPheNle S-MeCys, 69 mg of 1-hydroxybenzotriazole and 105 mg of dicyclohexylcarbodiimide in 10 ml of methylene chloride was stirred overnight at room temperature. The reaction mixture was filtered, washed with water and a saturated brine solution and the organic phase dried over sodium sulfate. Removal of the solvent in vacuo gave 212 mg of crude product, which was purified by chromatography on 22 g of silica gel using chloroform - methanol (99:1; v:v) as the eluent. The fractions containing the product were combined, concentrated and triturated to give 78 mg of pure product as a white solid.

$^1$H NMR (DMSO-d$_6$, 60 mHz, ppm partial) 2.05 (s, 3H, J=5Hz), 2.2-2.4 (d, 2H, J=5Hz), 3.3-3.4 (m, 4H), 3.50-3.60 (m, 4H), 3.85 (s, 3H), 7.2 (s, 5H).

PREPARATION 1

MorpholinocarbonylPheNle A. Norleucine benzyl ester

According to the general procedure outlined in J. Med. Chem. 1986, Vol. 30, p. 3575, 15.0 g norleucine (Nle) was mixed with 200 ml benzyl alcohol and cooled to 0° C. Thionyl chloride (25 ml) was added dropwise over 15 minutes and the mixture was slowly heated to 90° C. with a fierce evolution of SO$_2$ occurring at about 50° C. After 2 hours at 90° C. the mixture was cooled to 0° C. and 25 ml more thionyl chloride was added. The mixture was then heated again at 90° C. for 2 hours, cooled, diluted with 1.6 liters ether and stored overnight at 0° C. The crystals which formed were filtered, washed with ether and dried to give 23.1 g of a damp solid which was recrystallized from 1:10 ethanol-ether, using 23 ml ethanol. The filtered and dried solid weighed 17.1 g, TLC Rf 0.25 in System C (the spotted plate was exposed to ammonia vapor and dried prior to elution).

B. (S)-2-Isocyanato-3-phenylpropionic acid benzyl ester

According to the procedure of Lombardino et al. (J. Med. Chem. 1964, 7, 97) 18.0 g L-phenylalanine benzyl ester hydrochloride in 150 ml toluene was stirred at reflux under an atmosphere of phosgene for 1.5H, cooled and concentrated to give a solid which was recrystallized from 120 ml hexane to give 16.1 g of colorless needles.

Anal. Calcd for C$_{17}$H$_{15}$NO$_3$: C, 72.59; H, 5.37; N, 4.98. Found: C, 72.32; H, 5.35; N, 4.92. MP 68°-72° C. [alpha]$_D^{23}$ −80.4° (c=1.02, CHCl$_3$) IR (CHCl$_3$) 2250, 1750 cm$^{-1}$.

C. MorpholinocarbonylPhe benzyl ester

The product of Preparation 1B was dissolved in 5 ml dichloromethane, treated at 25° C. with 930 μl morpholine and after 30 minutes the mixture was concentrated fo a waxy solid which was recrystallized from hot 4:1 hexane-ethyl acetate, giving 1.92 g of the title substance, mp 87°-89° C. MS (chemical ionization, isobutane) 369 (MH+, base peak).

D. MorpholinocarbonylPhe 6 The product of

Preparation 1C (1.85 g) was dissolved in 30 ml absolute methanol and 5 ml acetic acid and shaken with 0.5 g 10% Pd/C for 1 hour under a 53 psi hydrogen atmosphere. The suspension was filtered, concentrated, co-evaporated three times with added toluene and dried to give 1.43 g of a colorless foam.

E. MorpholinocarbonylPheNle benzyl ester

Following the procedure for preparation and purification of the product of Example 1, 2.12 g of the product of Preparation 1A and 2.63 g of the product of Preparation 1C gave 3.30 g of the title substance as a colorless foam, TLC Rf 0.5 in ethyl acetate on silica, HPLC ret. time 3.27 minutes 97% of total absorption to 25 minutes in 70/30 MeCN-pH 2.1 0.1M phosphate.

F. MorpholinocarbonylPheNle

The product of Preparation ID (3.3 g) was shaken in 35 ml methanol and 7 ml acetic acid with 1.0g 10% Pd/C for 45 minutes, filtered through Celite, concentrated, co-evaporated several times with toluene and ether and dried to give 2.9 g of a colorless solid, TLC Rf 0.2 in System C.

PREPARATION 2

2R,4S,5S-6-Cyclohexyl-5-(t-butoxycarbonylamino)-2-(2'-chloro-2'-propenyl)-gamma-hexanolactone To a tetrahydrofuran solution containing 37.5 mmol of lithium diethylamide at −70° C. (prepared from 23.4 ml of 1.6M butyl lithium hexane and 4.26 g of diethyl amine in 50 ml of dry tetrahydrofuran) was added dropwise a solution of 4.67 g (15 mmol) of 4S,5S-6-cyclohexyl-5-(t-butoxycarbonylamino)-gamma hexanolactone in 25 ml of tetrahydrofuran. After 30 minutes at −78° C. a solution of 3.64 g (16 mmol) of 2-chloro-3-iodopropene in 25 ml of tetrahydrofuran was added dropwise at −70° C. After 2 hours the reaction mixture was quenched with 10 ml of a saturated ammonium chloride solution added dropwise at −78° C., and the resulting mixture allowed to warm to room temperature. The solvent was removed in vacuo and the residue extracted with with diethyl ether. The ether solution was washed with a 10% citric acid solution, a saturated sodium bicarbonate solution and a brine solution. The ether solution was then dried over magnesium sulfate and concentrated to give 6.83 g of an oil, which was chromatographed on silica gel using ethyl acetate-hexane as the eluent. The fractions containing the product were combined and concentrated to give 2.38 g of the desired product.

The NMR spectrum (CDCl₃) showed absorption at 1.4 (9H, s) ppm.

PREPARATION 3

Employing the procedure of Preparation A, and using the appropriate starting reagents, the following intermediates were synthesized:

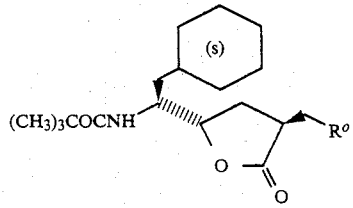

| R° |
|---|
| —CH=CH—CH₂Br |
| —C=CH₂<br>\|<br>Br |
| —CH=CHCl |
| —CH=C(CH₃)₂ |
| CH=CHCH₃ |
| C≡CH |

PREPARATION 4

2R,4S,5S-6-Cyclohexyl-5-(t-butoxycarbonylamino)-2-(4-azido-2-butenyl)-gamma-hexanolactone A solution of 710 mg (1.6 mmol) of 2R,4S,5S-6-cyclohexyl-5-(t-butoxycarbonylamino)-2-(4'-bromo-2'-butenyl)gamma-hexanolactone and 986 mg (15.2 mmol) of sodium azide in 75 ml of dimethylsulfoxide-water (2:1; v:v) was allowed to stir overnight at room temperature. The reaction was poured into 500 ml of water and the product extracted with ethyl acetate. The extracts were combined and washed successively with water and a brine solution, and were dried over magnesium sulfate. The solvent was removed in vacuo to give 73 mg of the desired product.

PREPARATION 5

2R,4S,5S-6-Cyclohexyl-5-amino-2-(2'-chloro-2'-propenyl)-gamma-hexanolactone hydrochloride A solution of 385 mg (1 mmol) of 2R,4S,5S-6-cyclohexyl-5-(t-butoxycarbonylamino)-2-(2'- chloro-2'-propenyl)-gamma-hexanolactone in 10 ml of 4.7N hydrogen chloride in dioxane was allowed to stir for 2 hours at room temperature. The solvent was removed in vacuo to give 331 mg of the desired amine hydrochloride.

PREPARATION 6

Using the procedure of Preparation 5, and employing the intermediates of Preparations 2, 3 and 4, the following intermediates were prepared:

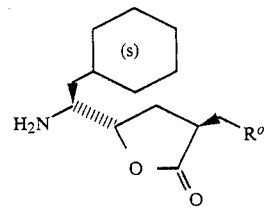

| R° |
|---|
| —C=CH₂<br>\|<br>Cl |
| CH=CHCH₂N₃ |
| —C=CH₂<br>\|<br>Br |
| —CH=CHCl |
| —CH=C(CH₃)₂ |
| CH=CHCH₃ |
| C≡CH |

PREPARATION 7

MorpholinocarbonylPhe S-MeCys

A. morpholinocarbonylPhe S-MeCys methyl ester
MorpholinocarbonylPhe (0.96 g) and S-MeCysOMe-HCl (0.55 g) were coupled using the water soluble reagent DEC, along with TEA and HBT as in Example 55. The reaction mixture was diluted with 100 mL EtOAc washed 2×35 mL 0.1N HCl and 2×35 mL 0.1 N NaOH. The organic phase was dried over MgSO₄, filtered and concentrated in vacuo. The crude product (1.15 g) was pure enough to be carried through NMR (300 MHz, CDCl₃) delta 2.00 (s, 3H), 3.72 (s, 3H), 4.58 (m, 1H), 4.65 (m, 1H).

B. morpholinocarbonylPhe S-MeCys
MorpholinocarbonylPhe S-MeCys methyl ester (1.15 g) was sponified with 300 mg K₂CO₃ in 30 ml MeOH, the reaction being stirred at 0° for 15 minutes and then at RT. The crude product (1.0 g) was used without further purification. NMR (300 MHz, CDCl₃), delta 2.03 (s, 3H), 4.63 (m, 1H), 4.77 (m, 1H).

We claim:
1. A compound of the formula

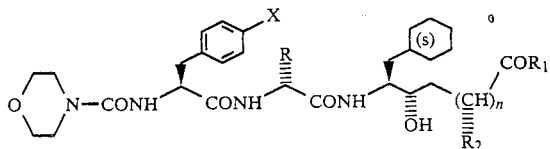

and a pharmaceutically acceptable salt thereof wherein X is hydrogen, methoxy or hydroxy; R is alkyl having one to six carbon atoms or methylthiomethyl; n is an integer of 1; $R_1$ is amino, alkylamino having from one to five carbon atoms, alkoxy having from one to three carbon atoms or 2-alkoxycarbonylpyrrolidin-1-yl said alkoxy having from one to three carbon atoms; and $R_2$ is alkyl having three to four carbon atoms —$CH_2CH(Cl)=CH_2$, —$CH_2CH=CH—CH_2N_3$, —$(CH_2)_4NH_2$, —$CH_2CH(Br)=CH_2$, —$CH_2CH=CHCl$, —$CH_2CH=C(CH_3)_2$, —$CH_2CH=CHCH_3$ or —$CH_2C≡CH$.

2. A compound of claim 1 wherein X is hydrogen and R is alkyl having three to four carbon atoms.

3. The compound of claim 2 wherein R is n-butyl, $R_1$ is methylamino and $R_2$ is i-butyl.

4. A compound of claim 1, wherein X is hydrogen and R is alkyl having three to four carbon atoms.

5. The compound of claim 6, wherein $R_1$ is methylamino and $R_2$ is —$CH_2CH(Cl)=CH_2$.

6. A method for treating hypertension in a mammal which comprises treating said mammal with an antihypertensive effective amount of a compound according to claim 1.

7. A pharmaceutical composition comprising an antihypertensive effective amount of a compound according to claim 1 and a pharmaceutically acceptable diluent or carrier.

8. A compound of the formula

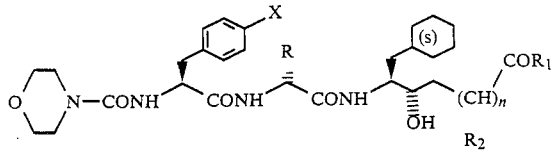

and a pharmaceutically acceptable salt thereof wherein X is hydrogen, methoxy or hydroxy; R is methylthiomethyl; n is an integer of 0; and $R_1$ is amino, alkylamino having from one to five carbon atoms, alkoxy having from one to three carbon atoms or 2-alkoxycarbonylpyrrolidin-1-yl said alkoxy having from one to three carbon atoms.

9. A compound of claim 8, wherein X is hydrogen and $R_1$ is alkoxy having one to three carbon atoms.

10. The compound of claim 9, wherein $R_1$ is methoxy.

11. A method for treating hypertension in a mammal which comprises treating said mammal with an antihypertensive effective amount of a compound according to claim 8.

12. A pharmaceutical composition comprising an antihypertensive effective amount of a compound according to claim 8 and a pharmaceutically acceptable diluent or carrier.

* * * * *